(12) United States Patent
Chang et al.

(10) Patent No.: US 10,752,947 B2
(45) Date of Patent: Aug. 25, 2020

(54) METHOD TO AMPLIFY TRANSVERSE TUNNELING CURRENT DISCRIMINATION OF DNA NUCLEOTIDES VIA NUCLEOTIDE SITE SPECIFIC ATTACHMENT OF DYE-PEPTIDE

(71) Applicant: SEAGATE TECHNOLOGY LLC, Cupertino, CA (US)

(72) Inventors: Thomas Young Chang, Menlo Park, CA (US); Philip L. Steiner, Los Altos, CA (US); Kim Yang Lee, Fremont, CA (US); David S. Kuo, Palo Alto, CA (US)

(73) Assignee: SEAGATE TECHNOLOGY LLC, Fremont, CA (US)

( * ) Notice: Subject to any disclaimer, the term of this patent is extended or adjusted under 35 U.S.C. 154(b) by 263 days.

(21) Appl. No.: 15/886,736

(22) Filed: Feb. 1, 2018

(65) Prior Publication Data
US 2018/0258480 A1    Sep. 13, 2018

Related U.S. Application Data

(60) Provisional application No. 62/469,393, filed on Mar. 9, 2017.

(51) Int. Cl.
| | | |
|---|---|---|
| *C12P 19/34* | (2006.01) | |
| *C12Q 1/6869* | (2018.01) | |
| *C40B 40/06* | (2006.01) | |

(52) U.S. Cl.
CPC ............ *C12Q 1/6869* (2013.01); *C40B 40/06* (2013.01); *B01J 2219/00722* (2013.01); *C12Q 2563/116* (2013.01); *C12Q 2563/119* (2013.01)

(58) Field of Classification Search
CPC ......... B01J 2219/00722; C12Q 1/6869; C12Q 2563/116; C12Q 2563/119; C40B 40/06

USPC ........................................................ 435/91.2
See application file for complete search history.

(56) References Cited

U.S. PATENT DOCUMENTS 9,410,923 B2    8/2016 Sauer et al.

OTHER PUBLICATIONS

Carson et al., Nanotechnology, 26(7), pp. 1-24, Jan. 2016.*
Alvarez et al., Frontiers in Genetics, 6 (213), 1-11, Jun. 2015.*
Ohshiro et al., PNAS, 103(1), 10-14, Jan. 2006.*
Heerema et al., Nature Nanotechnology, 11, 127-136, Feb. 2016.*
Ohshiro et al., Scientific Report, 2: 501, 1-7, Jul. 2012.*
Di Ventra, Massimiliano, et al., "Decoding DNA, RNA and peptides with quantum tunneling," Nature Nanotechnology, vol. 11, Feb. 2016, pp. 117-126.
Feng, Yanxiao, et al., "Nanopore-based Fourth-generation DNA Sequencing Technology," Genomics Proteomics Bioinformatics, 13 (2015), pp. 4-16.
Ivanov, A.P., et al., "DNA Tunneling Detector Embedded in a Nanopore," Nano Letters, 2011, 11, pp. 279-285.
Ke, Rongqin, et al., "Fourth Generation of Next-Generation Sequencing Technologies: Promise and Consequences," Human Mutation, vol. 37, No. 12, 2016, pp. 1363-1367.
Kulski, Jerzy K., "Next-Generation Sequencing—An Overview of the History, Tools, and 'Omic' Applications," http://dx.doi.org/10.5772/61964, 59 pages.

* cited by examiner

*Primary Examiner* — Cynthia B Wilder
(74) *Attorney, Agent, or Firm* — Holzer Patel Drennan (57) ABSTRACT

Apparatus and methods to identify nucleotides of a DNA strand. The method includes exposing the DNA strand to a first dye or peptide, attaching the first dye or peptide to a first type of nucleotide (A,T,C,G) of the DNA strand, the first dye or peptide changing a conductance of the first type of nucleotide to which the first dye or peptide is attached, and measuring a tunneling current signal for all nucleotides of the DNA strand, the changed conductance of the first type of nucleotide providing amplified tunneling current discrimination of the nucleotides of the DNA strand.

20 Claims, 9 Drawing Sheets

METHOD TO AMPLIFY TRANSVERSE TUNNELING CURRENT DISCRIMINATION OF DNA NUCLEOTIDES VIA NUCLEOTIDE SITE SPECIFIC ATTACHMENT OF DYE-PEPTIDE

RELATED APPLICATIONS

This application claims the benefit of the filing date of U.S. Provisional Application No. 62/469,393, filed on 9 Mar. 2017, and entitled METHOD TO AMPLIFY TRANSVERSE TUNNELING CURRENT DISCRIMINATION OF DNA NUCLEOTIDES VIA NUCLEOTIDE SITE SPECIFIC ATTACHMENT OF DYE-PEPTIDE, the disclosure of which is incorporated in its entirety by this reference.

SUMMARY

One aspect of the present disclosure relates to a method of identifying nucleotides of a DNA strand. The method includes exposing the DNA strand to a first dye or peptide, attaching the first dye or peptide to a first type of nucleotide (A,T,C,G) of the DNA strand, the first dye or peptide changing a conductance of the first type of nucleotide to which the first dye or peptide is attached, and measuring a tunneling current signal for all nucleotides of the DNA strand, the changed conductance of the first type of nucleotide providing amplified tunneling current discrimination of the nucleotides of the DNA strand.

The first type of nucleotide may be an A (Adenine) nucleotide or a C (Cytosine) nucleotide. The method may further include exposing the DNA strand to a second dye or peptide, and attaching the second dye or peptide to a second type of nucleotide (A,T,C,G) of the DNA strand, the second dye or peptide changing a conductance of the second type of nucleotide to which the second dye or peptide is attached. The changed conductance of the second type of nucleotide may provide amplified tunneling current discrimination of the nucleotides of the DNA strand when measuring the tunneling current signal for all nucleotides of the DNA strand. The change in conductance may be a reduction in conductance. The reduction in conductance may result in an increased tunneling current signal for the first type of nucleotide. The reduction in conductance may be to a conductance level that is less than a conductance for all other types of nucleotides of the DNA strand.

Another aspect of the present disclosure relates to a method of DNA sequencing. The method includes providing a plurality of channels, each channel comprising at least one tunneling electrode, exposing a first DNA strand to a first dye or peptide, and attaching the first dye or peptide to a first type of nucleotide (A,T,C,G) of the first DNA strand, the attached first dye or peptide changing a conductance of the first type of nucleotide, exposing a second DNA strand to a second dye or peptide, and attaching the second dye or peptide to a second type of nucleotide (A,T,C,G) of the second DNA strand, the attached second dye or peptide changing a conductance of the second type of nucleotide, and exposing a third DNA strand to a third dye or peptide, and attaching the third dye or peptide to a third type of nucleotide (A,T,C,G) of the third DNA strand, the attached third dye or peptide changing a conductance of the third type of nucleotide. The method also includes passing the first, second and third DNA strands through separate ones of the plurality of DNA sequencing channels, measuring a tunneling current for the nucleotides with attached dyes or peptides in each of the channels, the measured tunneling currents being used to identify a location of the nucleotides with attached dyes or peptides on each DNA strand, and determining a sequence for the nucleotides of the DNA strands using the identified locations for the nucleotides with attached dyes or peptides.

The plurality of channels may include four channels, and the method further includes exposing a fourth DNA strand to a fourth dye or peptide, and attaching the fourth dye or peptide to a fourth type of nucleotide (A,T,C,G) of the fourth DNA strand, the attached fourth dye or peptide changing a conductance of the fourth type of nucleotide, and passing the fourth DNA strand through one of the plurality of DNA sequencing channels. The plurality of DNA sequencing channels may include three DNA sequencing channels, and the plurality of DNA strands may include three DNA strands. The locations for the first, second and third types of nucleotides may be used to construct a partial DNA sequence, and locations for a fourth nucleotide may be determined by process of elimination. Changing the conductance of the first, second and third types of nucleotides may include reducing the conductance. The reduction in conductance may result in an increased tunneling current signal. The DNA strands may each have identical DNA sequencing.

Another aspect of the present disclosure relates to a DNA sequencing method that includes amplifying tunneling current discrimination of nucleotides of a DNA strand using attachment of dyes or peptides to at least one specific type of nucleotide (A,T,C,G) of the DNA strand. The dyes or peptides may change a conductance value for the nucleotide to which the dyes or peptides are attached, and the changed conductance may result in a changed tunneling current value for the nucleotides to which the dyes or peptides are attached. The type of nucleotide may be one of an A (Adenine) nucleotide or a C (Cytosine) nucleotide. The method may include determining at least a portion of a DNA sequence using the amplified transverse tunneling current discrimination. The method may include exposing the DNA strand to a first dye or peptide, attaching the first dye or peptide to a first type of nucleotide (A,T,C,G) of the DNA strand, the first dye or peptide changing the conductance of the first type of nucleotide to which the first dye or peptide is attached, and measuring a tunneling current signal for all nucleotides of the DNA strand, the changed conductance of the first type of nucleotide providing amplified tunneling current discrimination of the nucleotides of the DNA strand.

The method may include exposing the DNA strand to a second dye or peptide, and attaching the second dye or peptide to a second type of nucleotide (A,T,C,G) of the DNA strand, the second dye or peptide changing the conductance of the second type of nucleotide to which the second dye or peptide is attached. The change in conductance may be a reduction in conductance, the reduction in conductance providing an increased tunneling current signal for the first type of nucleotide.

The foregoing has outlined rather broadly the features and technical advantages of examples according to this disclosure so that the following detailed description may be better understood. Additional features and advantages will be described below. The conception and specific examples disclosed may be readily utilized as a basis for modifying or designing other structures for carrying out the same purposes of the present disclosure. Such equivalent constructions do not depart from the scope of the appended claims. Characteristics of the concepts disclosed herein, including their organization and method of operation, together with associated advantages will be better understood from the following description when considered in connection with the accompanying figures. Each of the figures is provided for the purpose of illustration and description only, and not as a definition of the limits of the claims.

BRIEF DESCRIPTION OF THE DRAWINGS

A further understanding of the nature and advantages of the present disclosure may be realized by reference to the following drawings. In the appended figures, similar components or features may have the same reference label. Further, various components of the same type may be distinguished by following a first reference label with a dash and a second label that may distinguish among the similar components. However, features discussed for various components—including those having a dash and a second reference label—apply to other similar components. If only the first reference label is used in the specification, the description is applicable to any one of the similar components having the same first reference label irrespective of the second reference label.

DETAILED DESCRIPTION

Despite considerable efforts, DNA sequencing today still suffers from high costs and low speeds. To address all these issues, various methods have been proposed over the past decade that would allow individual DNA strands to be read directly. Among these, nanopore and nanochannel based approaches have emerged as the most promising. However, many challenges exist related to fabricating a channel and/or pore opening that is sufficiently small to limit passage to a single DNA strand, and there is no such report of a relatively mature method that address this unmet need.

Direct DNA sequencing has drawn attention due to its advantages on long read length, high throughput and low cost. Direct DNA sequencing methods using transverse tunneling current measurement have been studied extensively in literature. However, a manufacturably viable direct DNA sequencing device with required dimensions for the gap between the nanoelectrodes, nor methods for creating such a device, have not been discovered. Conventional MEMS and nanofabrication methods are inadequate for creating the required structure.

The present disclosure generally relates to DNA sequencing, and more particularly relates to DNA sequencing devices having nanochannels and nanoelectrodes, and related methods of fabricating such devices. The present disclosure may also relate to DNA sequencing using such devices. The device may include a nanofluidic channel through which DNA strands can be guided through a subnanometer electrode gap. Also disclosed here are DNA sequencing devices that are configured to read DNA using tunneling current and based on ionic current measurement through a subnanometer orifice, which is expected to be faster and more accurate than existing products and methods.

The general approach to DNA sequencing using tunneling electrodes involves electrically driving DNA and RNA strands through a nanopore or narrow channel via ionic flow or driven by a pressure gradient. As the strand pass a high resolution sensor (e.g., electrode) embedded inside the channel, the high spatial resolution sensor measures the unique properties of the individual bases (A,T,C,G). One type of sensor would consist of a conductive electrode that measures the unique tunneling currents (e.g., based on conductance of the nucleotides) associated with the nucleotide, thereby identifying and resolving the four unique nucleotide types.

Figure 1A:
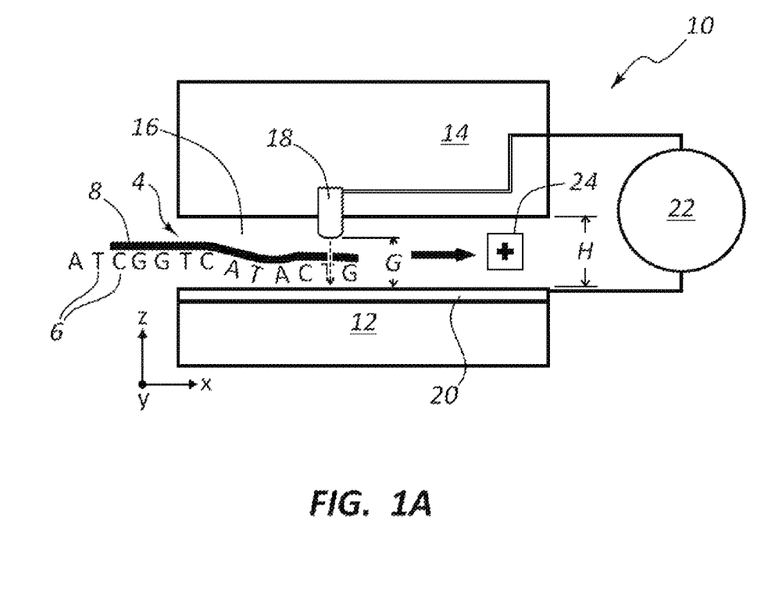
FIG. 1A schematically illustrates a DNA sequencing device in accordance with the present disclosure.
Figure 1B:
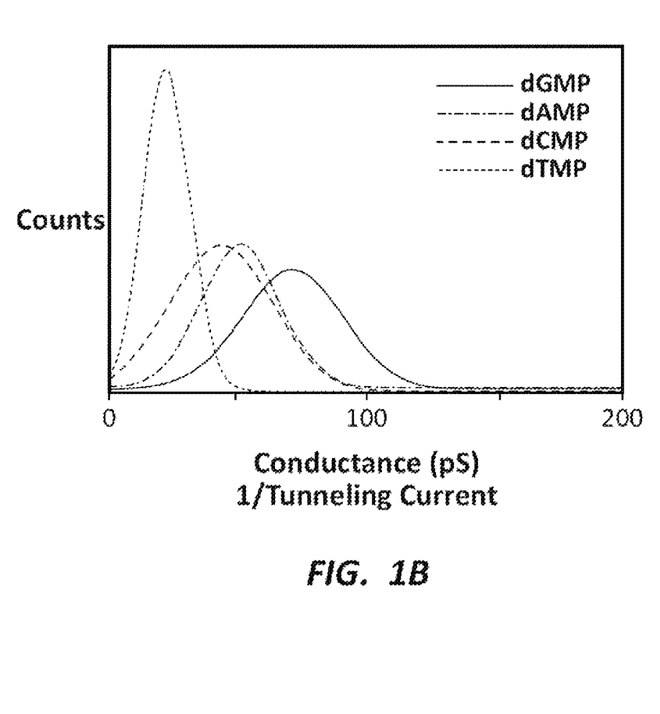
FIG. 1B is a graph showing conductance for nucleotides of a DNA strand passing through the DNA sequencing device shown in FIG. 1A.

FIG. 1 schematically illustrates an example DNA sequencing device 10 used to measure a transverse tunneling signal as a DNA strand 4 translates through a nanochannel 16 of the device 10. The measured tunneling current signals for some of the nucleotides 6 of the DNA strand 4 may overlap (e.g., see the current signals for nucleotides A and C in the graph of FIG. 1B), thus making discrimination of the nucleotides 6 difficult since the tunneling current associated with each nucleotide is not entirely unique. The tunneling current may be represented as a conductance measurement (pS), which is an inverse of the tunneling current, as shown in the graph of FIG. 1B. FIG. 1B shows that the peaks of the conductance measured for some of the nucleotides A,T,C,G may be positioned close enough to each other that it is difficult to distinguish between them.

Some types of dyes and peptides, which attach to the nucleotides 6 of a DNA strand 4, may change the conductance of the particular nucleotides 6 to which the dye/peptide is attached. Exposing a single strand DNA 4 to a site specific dye or peptide may result in attachment of the dye/peptide to a specific nucleotides 6, and the conductance of that nucleotide is changed. In some cases, the conductance of that nucleotides 6 is changed (e.g., reduced) dramatically, thus leading to a more easily identified difference in the tunneling current signal for that specific nucleotides 6.

Referring again to FIG. 1A, the DNA sequencing device 10 includes a substrate 12, an upper layer 14, a nanochannel 16, first and second electrode members 18, 20, and a controller or pre-amp 22 connected to the electrode members 18, 20. The nanochannel 16 has a height H typically in the range of about 5 nm to about 50 nm, and more particularly in the range of about 3 nm to about 20 nm. A gap G between the first and second electrode members 18, 20 typically is in the range of about 0.3 nm to about 5 nm, more particularly about 0.3 nm to about 2 nm, and typically about 1 nm. In some embodiments, the gap G may be variable by moving one or more of the first and second electrodes 18, 20 relative to the other.

During use, a DNA strand 4 is drawn into the nanochannel by electrophoresis forces. The DNA strand 4 may have a negative charge (e.g., a backbone 8 and/or the nucleotides 6 may carry a negative charge), and a positive energy source 24 is positioned downstream of the first and second electrodes 18, 20, such as outside of the nanochannel 16, to draw the DNA strand 4 through the gap G where the tunneling current is measured using the electrode members 18, 20 and the controller/pre-amp 22. The output from the pre-amp 22 may be plotted on a graph such as the graph shown in FIG. 1B. A range of conductance values for each type of nucleotide 6 may be generally known. However, in some cases, the average conductance for at least some of the nucleotides (e.g., types A and C as shown in FIG. 1B) may be close enough together that it is difficult to distinguish between the tunneling current measurements for those two types of nucleotides. By attaching a dye or peptide to one of the nucleotide types (e.g., type A or C), the conductance of the nucleotide carrying the attached dye/peptide may be significantly different from the closest nucleotide type and may be spaced from all other nucleotide types, thereby making it easier to identify and distinguish the nucleotide carrying the dye/peptide from the other nucleotides.

Figures 2A, 2B:
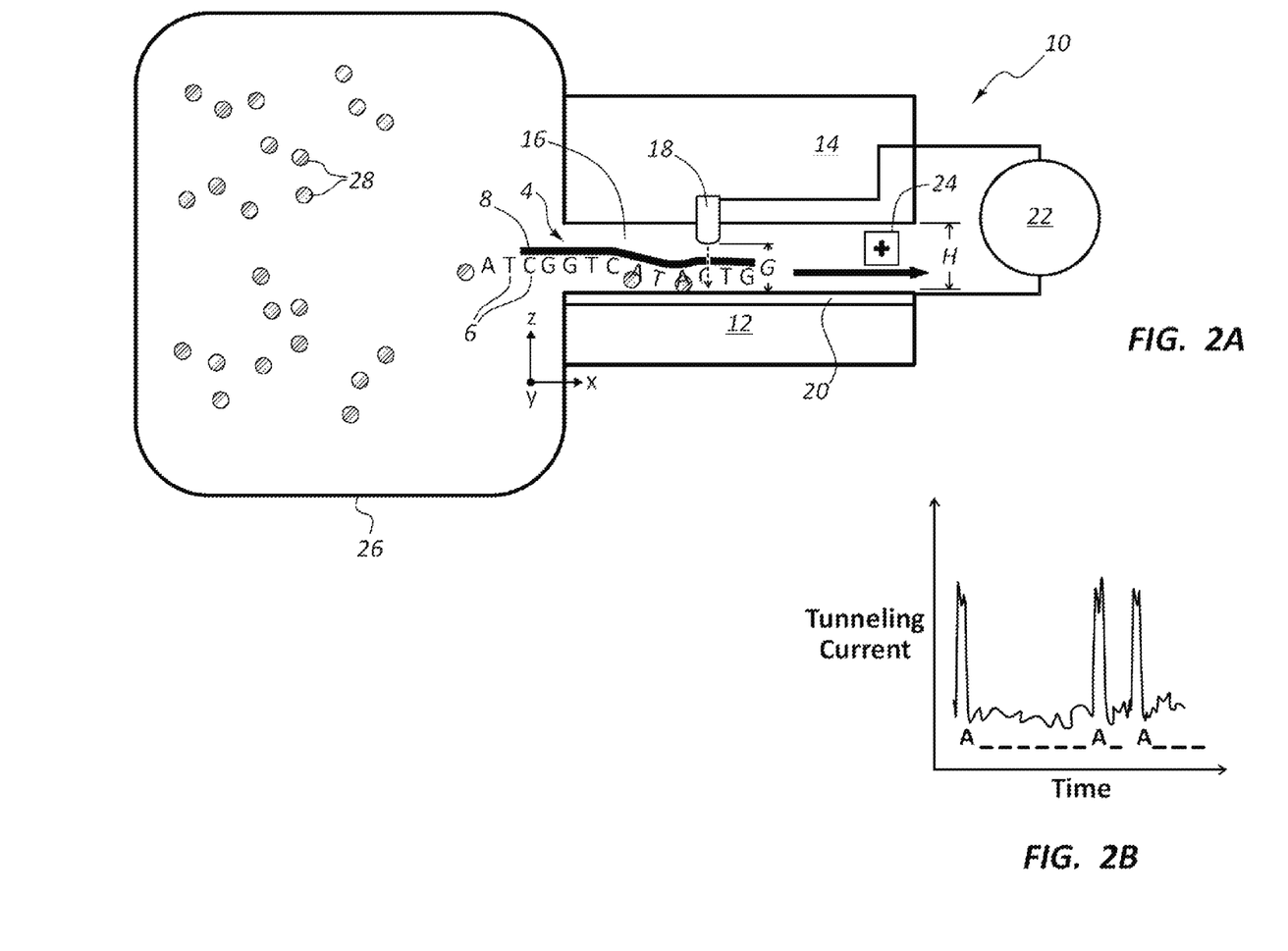
FIG. 2A schematically illustrates the DNA sequencing device of FIG. 1A with a dye/peptide reservoir and dye/peptide attached to specific nucleotides of a DNA strand.
FIG. 2B is a graph showing measured tunneling current for the nucleotides of the DNA strand passing through the DNA sequencing device shown in FIG. 2A.

Referring to FIGS. 2A and 2B, the nanochannel 16 of the DNA sequencing device 10 is arranged in flow communication with a reservoir 26 that holds at least one DNA strand 4 and a plurality of dye/peptide molecules 28. The dyes/peptides 28 attaches only to an "A" nucleotide on the DNA strand 4. The tunneling current signal measured for each site A on the DNA strand typically will be measurably, and sometimes significantly, different from the tunneling current signals for the remaining nucleotides 6 (e.g., C,T,G). This may result in an enhanced tunneling current contrast between the modified nucleotides A as compared to the remaining nucleotides C,T,G.

FIG. 2B is a graph showing tunneling current signals for the nucleotides 6 of the DNA strand 4 shown in FIG. 2A. The graph of FIG. 2B shows the increase in tunneling current for the A nucleotide due to the modification (e.g., attachment of the dye/peptide 28) at the nucleotides A, which increases conductance (and reduces the tunneling current) for the A nucleotides. The location of nucleotide A on DNA strand can be easily detected as a result of the modification using the dye/peptide 28.

Figure 3A:
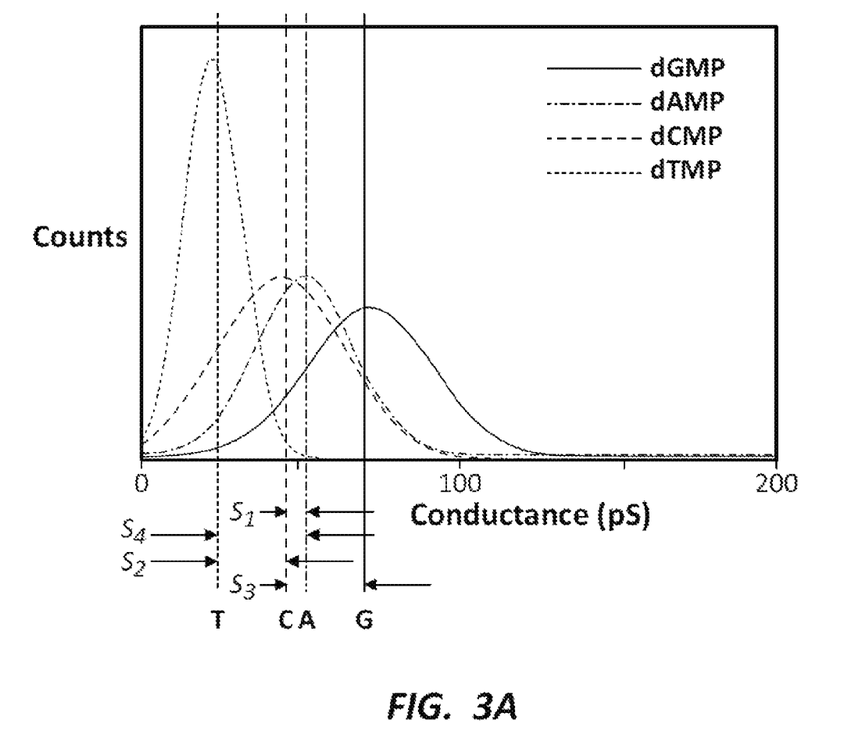
FIG. 3A is a graph showing example conductance values for nucleotides of a DNA strand.

FIG. 3A is a graph showing a median conductance and how it influences a measured value of the tunneling current for each nucleotide type (A,T,C,G). The C and A nucleotides 6 have the smallest conductance separation $S_1$, which results in the most difficult two nucleotides to distinguish from each other. The C and T nucleotides are separated a distance $S_2$. The A and G nucleotides are separated a distance $S_3$. The A and T nucleotides are separated a distance $S_4$. In one embodiment, a nucleotide specific dye/peptide may be attached to either the C or A nucleotide to reduce the conductance of that nucleotide and increase the tunneling current for that nucleotide (e.g., site on the DNA strand), as discussed above. Using the dye/peptide in this way may provide a more distinctive separation of conductance levels between the four nucleotide types and may provide a greater increase in tunneling current separation signal-to-noise ratio (SNR).

Figure 3B:
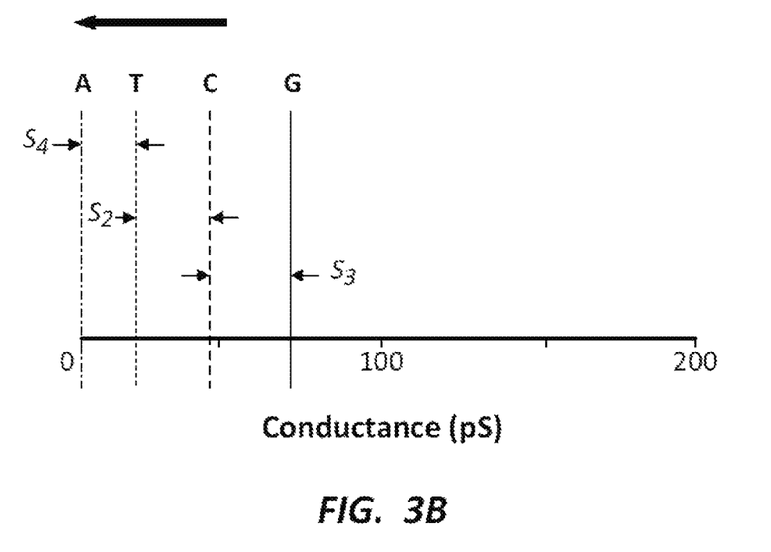
FIG. 3B shows shifting of a conductance value for one of the nucleotides shown in FIG. 3A as a result of attachment to a dye/peptide.

FIG. 3B illustrates the effective of site-specific dye/peptides being attached to only the A nucleotide. The conductance of the A nucleotide is reduced to a point that there is separation between the C and A nucleotides to include the distance $S_1$, and also separation between the A nucleotide and all other nucleotides (T,C,G). In some embodiments, the use of a dye/peptide changes the conductance of a particular nucleotide to a level that is either above or below the conductance level of all of the remaining nucleotides. In some embodiments, the distance $S_1$ has substantially increased, and the distances $S_2$-$S_4$ are substantially equal to each other. In the example of FIGS. 3A and 3B, attaching the dye/peptide to the C nucleotide may effectively generate similar results as attaching the dye/peptide to the A nucleotide.

Figure 4A:
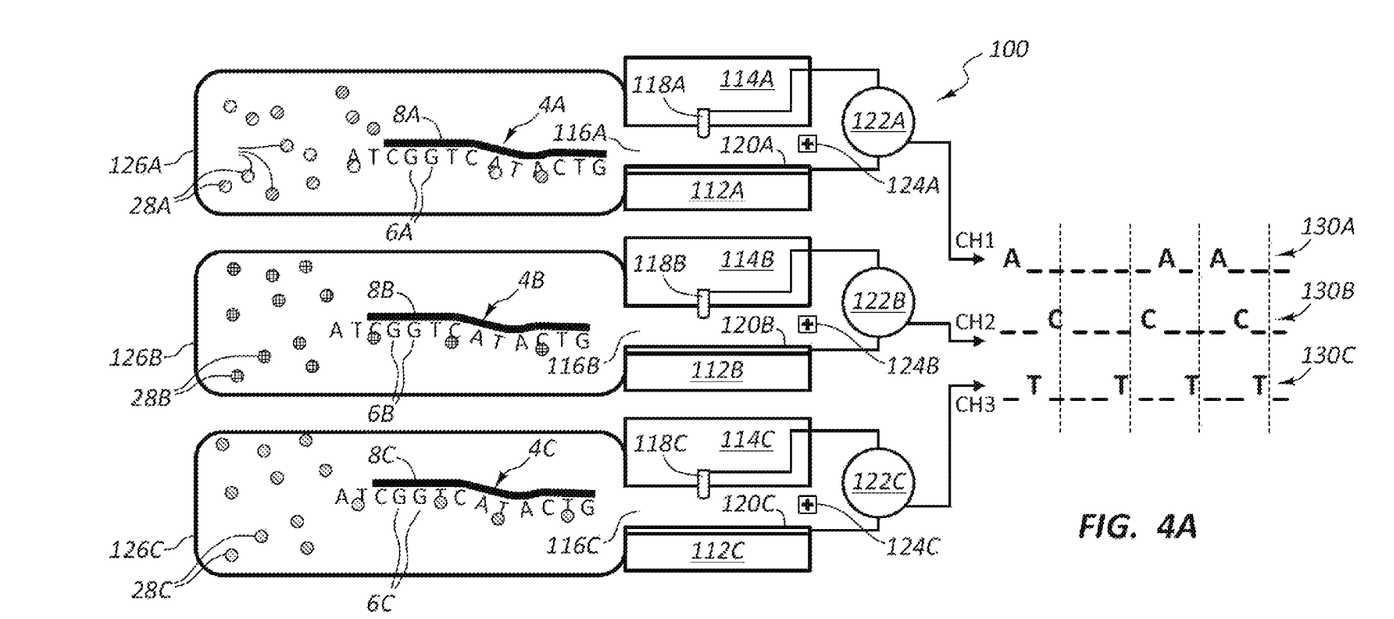
FIG. 4A schematically illustrates a three (3) channel DNA sequencing device in accordance with the present disclosure, each channel being associated with a different dye/peptide, and a partial sequence for each channel.

Other embodiments may provide for DNA sequencing devices having multiple channel configurations that provide increased accuracy of the DNA sequencing process. In one example, a DNA sequencing device 100 includes three (3) channels to read back the modified DNA strand and reconstruct the original DNA sequence. FIG. 4A illustrates a three-channel configuration in which each channel measures a single type of nucleotide location and gathers enough signals to reconstruct a four-letter sequence in the DNA strand.

The DNA sequencing device 100 includes substrates 12A-12C, upper layers 114A-114C, nanochannels 116A-116C, and pairs of first and second electrodes 118A-118C and 120A-120C. A separate controller or pre-amp 122A-122C is associated with each of the nanochannels 116A-116C, respectively. An energy source 124A-124C drives a DNA strand 4A-4C through the nanochannels 116A-116C, respectively. A separate reservoir 126A-126C is associated with each of the nanochannels 116A-116C, respectively. The reservoirs 126A-126C retain separate dyes/peptides 128A-128C, respectively, which attach to different nucleotide 6A-6C, of respective DNA strands 4A-4C.

Figure 4B:
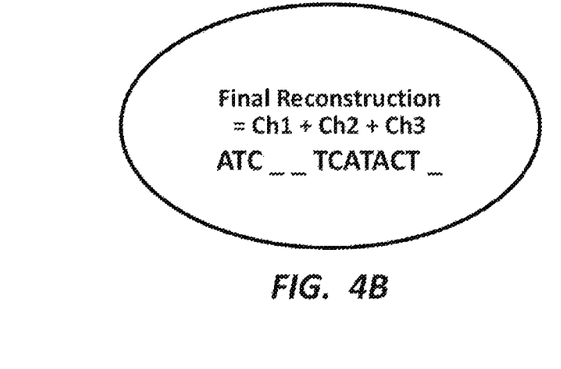
FIG. 4B illustrates a reconstruction of a DNA sequence based on the partial sequences from the channels of FIG. 4A.

As further shown in FIG. 4A, the tunneling current is determined for the nucleotide type to which the dye/peptide is attached for each respective nanochannel 116A-116C and provided as a partial sequence 130A-130C in association with each of the channels CH1-CH3, respectively. The partial sequences 130A-130C may be combined as a final reconstruction as shown in FIG. 4B. The final reconstruction provides the combination of partial sequences 130A-130C received at each of the channels CH1-CH3. By determining the sequence of three of the four nucleotide types of a given DNA strand, any remaining gaps in the DNA sequence are known to be filled by the nucleotide type that has not been targeted with a dye/peptide from the reservoirs 126A-126C. In the case of the final reconstruction shown in FIG. 4B, the gaps in the sequence are known to be filled by the nucleotide type G.

Multiple channel configurations may make it possible to increase the accuracy of the DNA sequencing process by using this basic approach. This approach may significantly increase the signal-to-noise ratio (SNR) of a single type of nucleotide in each channel. The entire DNA sequence may be reconstructed using the combined measure values for each channel output in a post-processing step.

Figures 5A, 5B:
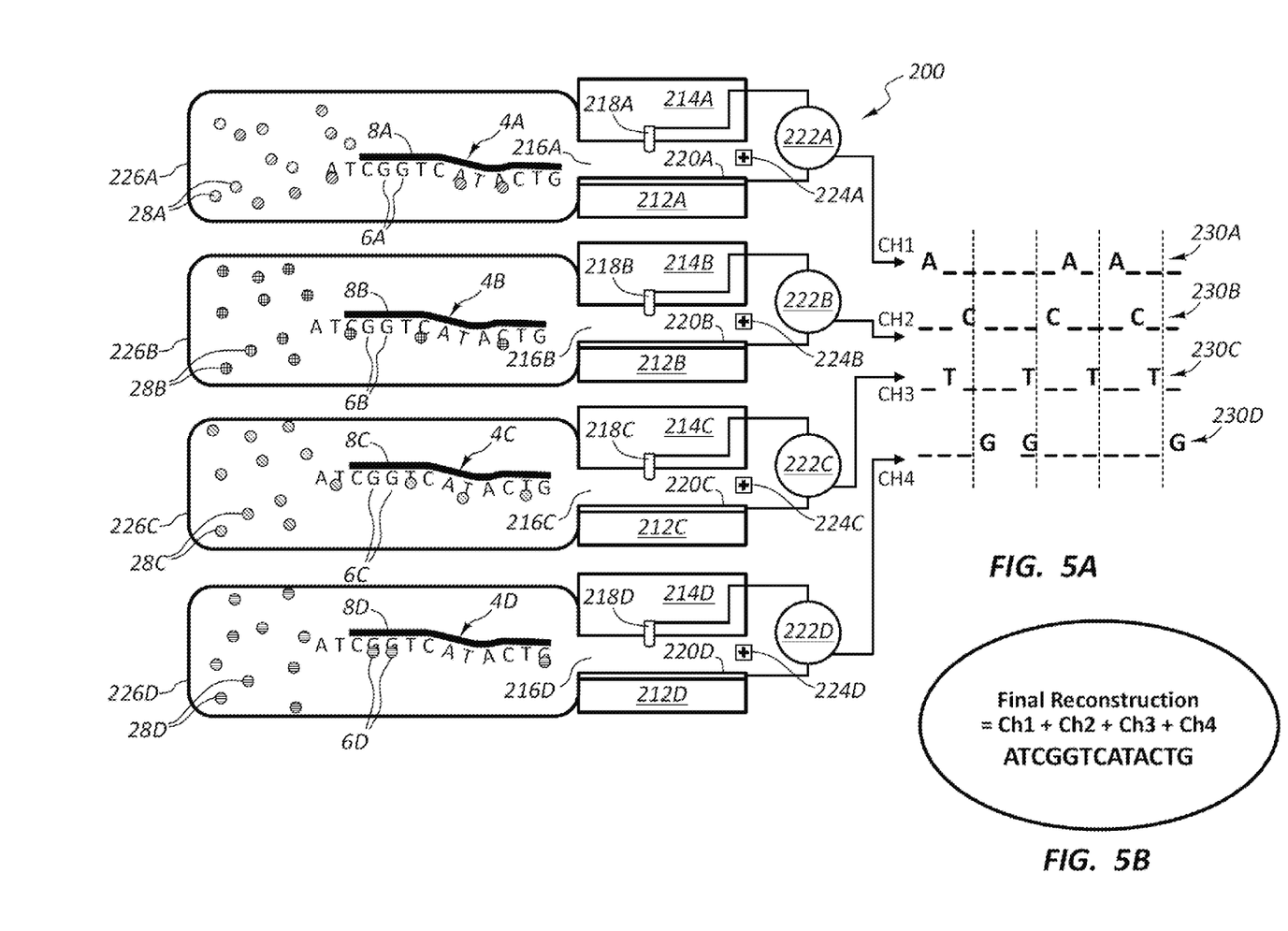
FIG. 5A schematically illustrates a four (4) channel DNA sequencing device in accordance with the present disclosure, each channel being associated with a different dye/peptide.
FIG. 5B illustrates a reconstruction of a DNA sequence based on the partial sequences from the channels of FIG. 5A.

A DNA sequencing device may contain more than three channels for a four-letter sequence in the DNA strand. A DNA sequencing device having more than three channels may add signal redundancy to further improve the reconstruction accuracy. FIG. 5A illustrates a four-channel DNA sequencing device 200 that provides such signal redundancy. The DNA sequencing device 200 includes substrates 212A-212D, upper layers 214A-214D, separate nanochannels 216A-216D, first and second electrode pairs 218A-218D and 220A-220D, and a controller or pre-amp 222A-222D associated with each pair of electrodes 218, 220. An energy source 224A-224D is used to draw a DNA strand through each of the respective nanochannels 216A-216D using electrophoresis. A reservoir 226A-226D is associated with each of the nanochannels 216A-216D, respectively. The reservoirs 226A-226D carry separate dyes/peptides 228A-228D, which are intended to attach to separate nucleotides A,T,C,G for the DNA strands 4A-4D, respectively.

In operation, the DNA sequencing device 200 determines a tunneling current for each of the nucleotides 6A-6D to which the dyes/peptides 228A-228D are attached to provide a plurality of partial sequences 230A-230D via channels CH1-CH4, respectively. The partial sequences 230A-230D may be combined as shown in FIG. 5 to create a final reconstruction. The final reconstruction may be carried out in a post-processing restructuring step that may result in a more accurate sequencing output as compared to the outputs available via DNA sequencing devices 10 and 100 described herein, and other known types of DNA sequencing devices and methods.

In other embodiments, a single one of the reservoirs associated with a DNA sequencing device may retain more than one type of dye/peptide, wherein each separate dye/peptide may be configured to attach to a single type of nucleotide of the DNA strands. The nucleotides with the attached dye/peptide may have a specific tunneling current that is unique as compared to the tunneling currents of all other nucleotides. The use of multiple dyes/peptides may provide a way to customize the tunneling current associated with each nucleotide in such a way to provide improved discrimination between the tunneling currents for each type of nucleotide, and may result in a more accurate sequencing output as compared to using a single type of dye/peptide.

In at least some embodiments, a separate dye/peptide for attachment to each of the four nucleotide types A,T,C,G may be included in a single reservoir. In still further embodiments, some reservoirs may carry a single or multiple dyes/peptides, whereas other reservoirs may include one or more other types of dyes/peptides for a different nanochannel in a given DNA sequencing device. Later reconstruction of a plurality of partial sequences may result in a final reconstruction with improved accuracy and/or redundancy.

In one example, a DNA sequencing device includes two nanochannels with a separate reservoir carrying one or two different types of peptides in each reservoir. All of the dyes/peptides used in both reservoirs may attach to different nucleotide types A,T,C,G. Each nanochannel may be associated with electrodes that measure the tunneling electrode and determine a sequence of one or two nucleotides as part of a partial sequence. The partial sequences may be combined to create a final reconstruction of a completed DNA sequence.

Various dyes and peptides may be used for the DNA sequencing devices and methods disclosed herein. Some example dyes and peptides include, for example, a peptide nucleic acid (PNA). Other examples may exist. PNAs may have relatively strong affinity, stability, and specificity to bonding to single strand DNA as compared to natural DNA nucleotides.

Figure 6:
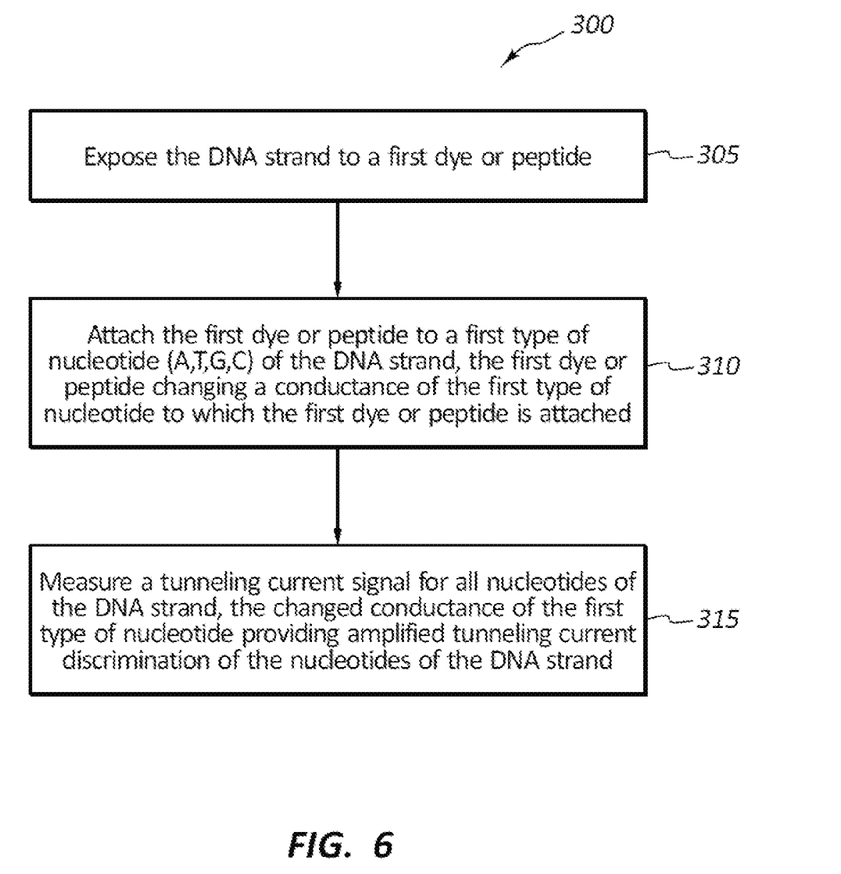
FIG. 6 is a flow diagram related to an example method in accordance with the present disclosure.

Various methods and processes are possible in accordance with the principles of the present disclosure. FIG. 6 illustrates method steps of an example method 300 for identifying nucleotides of a DNA strand. The method 300 includes, at block 305, exposing a DNA strand to a first dye or peptide. Block 310 includes attaching the first dye or peptide to a first type of nucleotide (A,T,C,G) of a DNA strand, wherein the first dye or peptide changes a conductance of the first type of nucleotide to which it is attached. Block 315 includes measuring a tunneling current signal for all nucleotides of the DNA strand, wherein the change in conductance of the first type of nucleotide provides amplified tunneling current discrimination of a nucleotide of the DNA strand.

The method 300 may also include providing the first type of nucleotide as an A (Adenine) nucleotide or a C (Cytosine) nucleotide. Method 300 may further include exposing the DNA strand to a second dye or peptide, attaching the second dye or peptide to a second type of nucleotide of a DNA strand, the second dye or peptide changing the conductance of the second type of nucleotide, wherein the changed conductance of a second type of nucleotide provides amplified tunneling current discrimination of the nucleotides of the DNA strand when measuring the tunneling current signal for all nucleotides of the DNA strand. The change in conductance may be a reduction in conductance. The reduction in conductance may result in an increased tunneling current signal for the first type of nucleotide. A reduction in conductance may be to a conductance level that is less than a conductance for all other types of nucleotides of the DNA strand.

Figure 7:
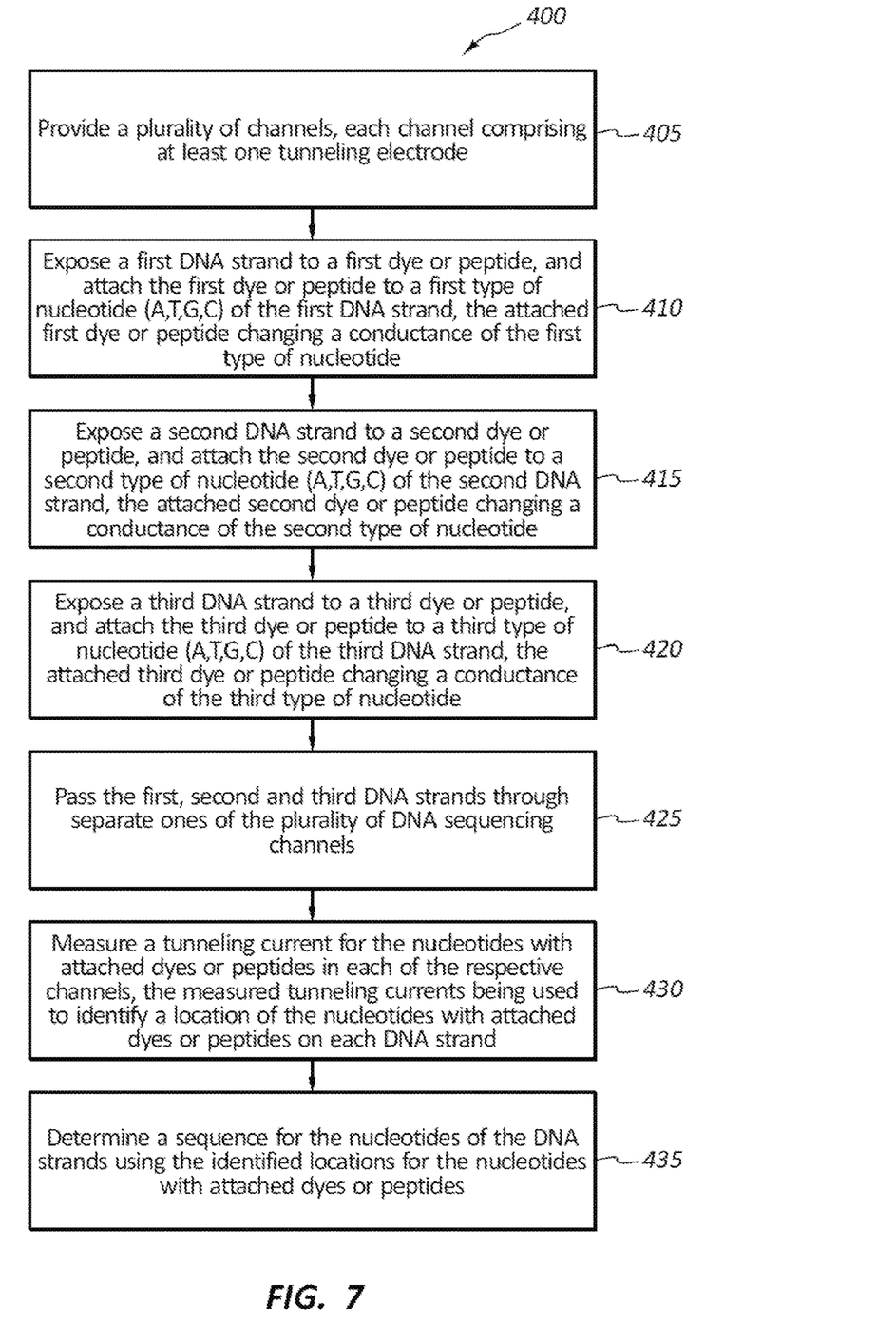
FIG. 7 is a flow diagram related to an example method in accordance with the present disclosure.

FIG. 7 is directed to a method 400 of DNA sequencing. The method 400 includes, at block 405, providing a plurality of channels, wherein each channel comprises at least one tunneling electrodes. Block 410 includes exposing a first DNA strand through a first dye or peptide, and attaching the first dye or peptide to a first type of nucleotide (A,T,C,G) of the first DNA strand, the attached first dye or peptide changing a conductance of the first type of nucleotide. Block 415 includes exposing a second DNA strand to a second dye or peptide, and attaching the second dye or peptide to a second type of nucleotide (A,T,C,G) of the second DNA strand, the attached second dye or peptide changing a conductance of the second type of nucleotide. Block 420 includes exposing a third DNA strand through a third dye or peptide, and attaching the third dye or peptide to a third type of nucleotide (A,T,C,G) of the third DNA strand, the attached third dye or peptide changing a conductance of the third type of nucleotide. Block 425 includes passing the first, second, and third DNA strands through separate ones of the plurality of DNA sequencing channels. Block 430 includes measuring a tunneling current for the nucleotides with attached dyes or peptides in each of the channels, the measured tunneling currents being used to identify location of the nucleotides with attached dyes or peptides on each of the DNA strands. Block 435 includes determining a sequence for the nucleotides of the DNA strands using the identified locations for the nucleotides with attached dyes or peptides.

The method 400 may also include providing the plurality of channels with four channels, and exposing a fourth DNA strand to a fourth dye or peptide, attaching the fourth dye or peptide to a fourth type of nucleotide (A,T,C,G) of the fourth DNA strand, the attached fourth dye or peptide changing a conductance of the fourth type of nucleotide, and passing the fourth DNA strand through one of the plurality of DNA sequencing channels. The method 400 may provide that the plurality of DNA sequencing channels includes three DNA sequencing channels, and the plurality of DNA strands including three DNA strands. The determined locations of the first, second, and third types of nucleotides may be used to construct a partial DNA sequence, and locations for the fourth nucleotide are determined by process of elimination. Changing the conductance of the first, second, and third types of nucleotides may include reducing the conductance. The reduction in conductance may result in an increased tunneling current signal. The DNA strands may each have identical DNA sequencing.

Figure 8:
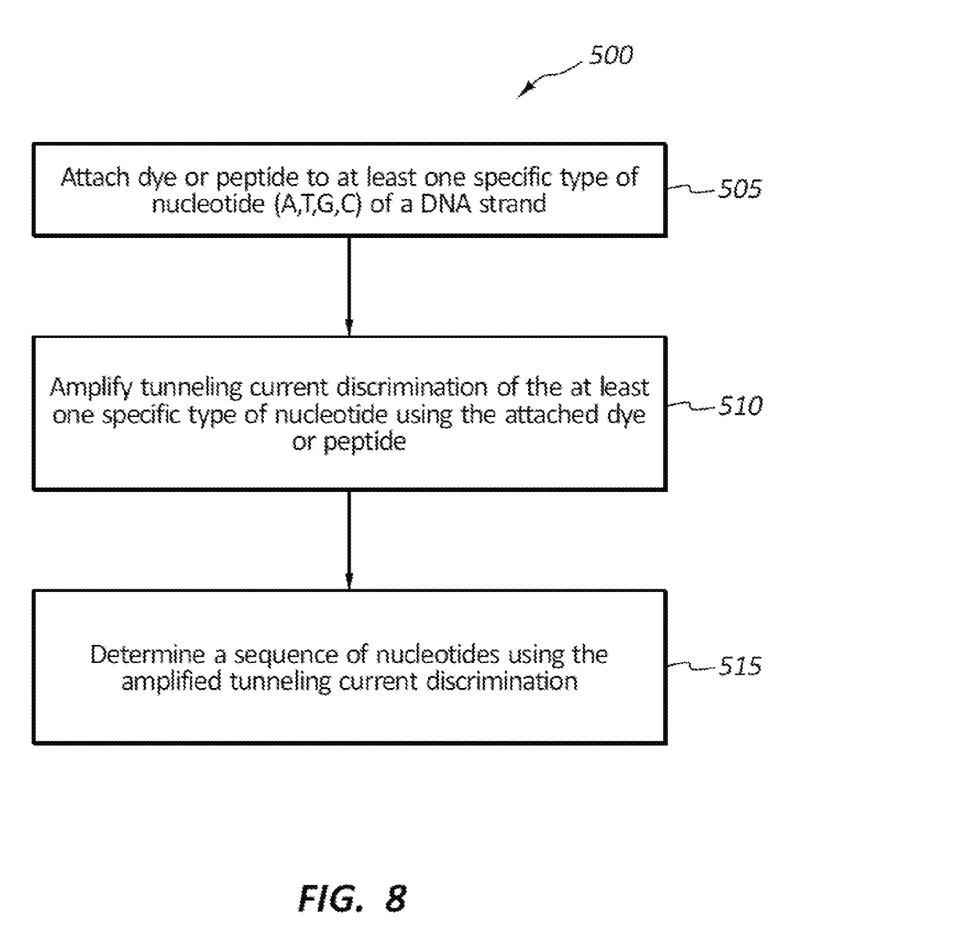
FIG. 8 is a flow diagram related to an example method in accordance with the present disclosure.

FIG. 8 illustrates steps of a method 500 for DNA sequencing. Block 505 includes attaching a dye or peptide to at least one specific type of nucleotide (A,T,C,G) of a DNA strand. Block 510 includes amplifying tunneling current discrimination of the at least one specific type of nucleotide using the attached dye or peptide. Block 515 includes determining a sequence of nucleotides using the amplified tunneling current discrimination.

The method 500 may provide that the dyes or peptides change a conductance value of the nucleotide to which the dyes or peptides are attached, and the changed conductance results in a changed tunneling current value for the nucleotides to which the dyes or peptides are attached. Method 400 may also provide that the type of nucleotide is one of an A (Adenine) nucleotide or a C (Cytosine) nucleotide. The method 500 may include determining at least a portion of a DNA sequence using an amplified transverse tunneling current discrimination. The method 500 may include exposing the DNA strand to a first dye or peptide, attaching the first dye or peptide to a first type of nucleotide of the DNA strand, the first dye or peptide changing the conductance of the first type of nucleotide to which the first dye or peptide is attached, and measuring a tunneling current signal for all nucleotides of the DNA strand, the changed conductance of the first type of nucleotide providing amplified tunneling current discrimination of the nucleotides of the DNA strand.

The method 500 may include exposing the DNA strand to a second dye or peptide, attaching the second dye or peptide to a second type of nucleotide of the DNA strand, the second dye or peptide changing the conductance of the second type of nucleotide to which the second dye or peptide is attached. The change in conductance may be a reduction in conductance, and the reduction in conductance provides an increased tunneling current signal for the first or second type of nucleotide.

Figure 9:
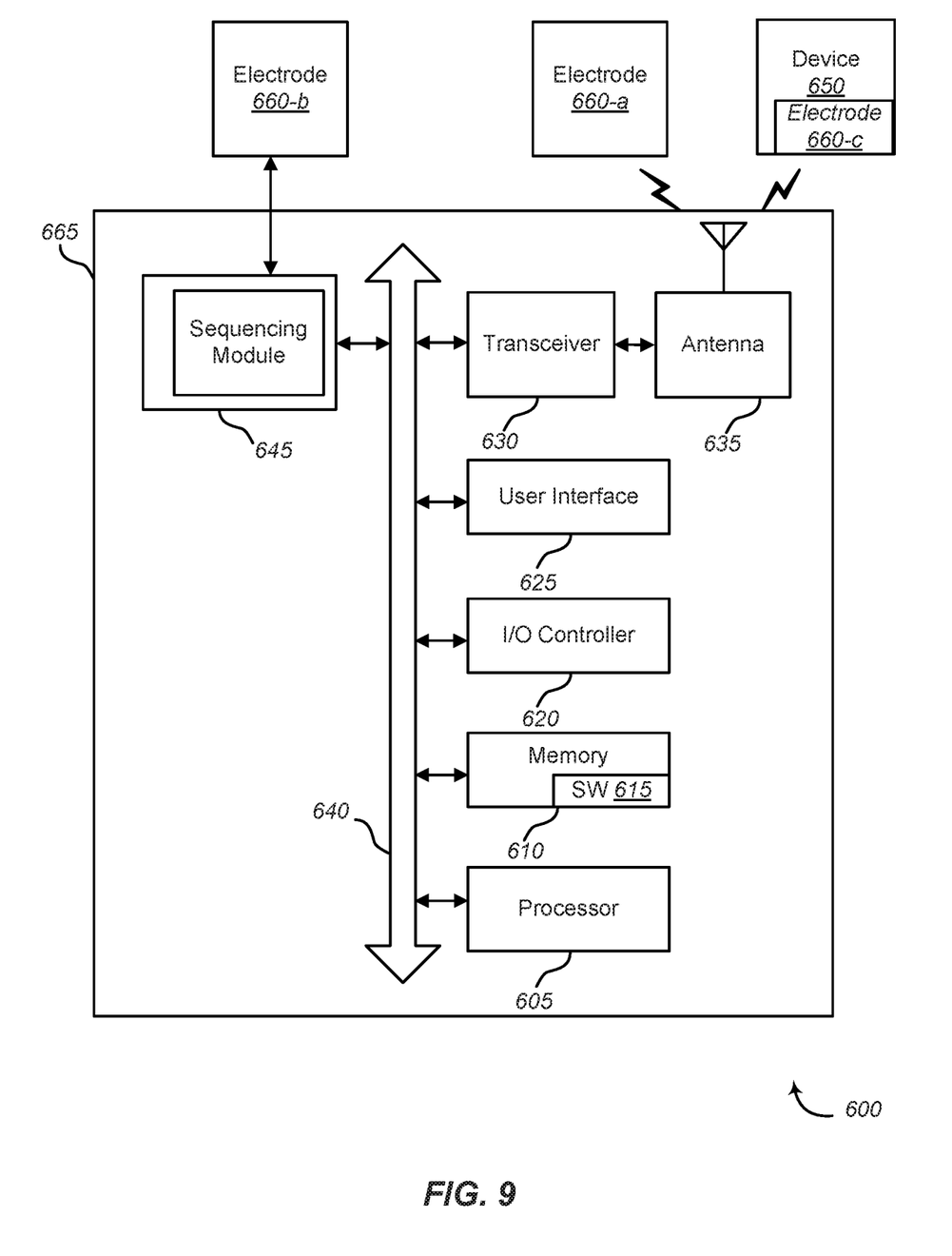
FIG. 9 shows a diagram of a system in accordance with various aspects of this disclosure.

FIG. 9 shows a system 600 for use with the DNA sequencing devices and systems shown in FIGS. 1-5. System 600 may include a control panel 665. Control panel 665 may be equivalent at least in part to a controller, control unit, processor or the like for use with the devices described above with reference to FIGS. 1-5. Control panel 665 may include sequencing module 645. The sequencing module 645 may provide communications with one or more electrodes 660 (also referred to as sensors or devices) directly or via other communication components, such as a transceiver 630 and/or antenna 635. The electrodes 660 may represent one or more of the electrodes 126, 206, or pairs of such electrodes in any of the embodiments described above. The sequencing module 645 may perform or control various operations associated with, for example, the electrodes 126, 206, actuator 208, controller, or other components of the DNA sequencing devices and related systems as described above with reference to FIGS. 1-7.

Control panel 665 may also include a processor module 605, and memory 610 (including software/firmware code (SW) 615), an input/output controller module 620, a user interface module 625, a transceiver module 630, and one or more antennas 635 each of which may communicate, directly or indirectly, with one another (e.g., via one or more buses 640). The transceiver module 630 may communicate bi-directionally, via the one or more antennas 635, wired links, and/or wireless links, with one or more networks or remote devices. For example, the transceiver module 630 may communicate bi-directionally with one or more of device 650 and/or electrodes 660-a, 660-c. The device 650 may be components of the DNA sequencing devices and related systems and devices described with reference to FIGS. 1-7, or other devices in communication with such systems and devices. The transceiver 630 may include a modem to modulate the packets and provide the modulated packets to the one or more antennas 635 for transmission, and to demodulate packets received from the one or more antennas 635. In some embodiments (not shown) the transceiver may be communicate bi-directionally with one or more of device 650, remote control device 655, and/or electrodes 660-a, 660-c through a hardwired connection without necessarily using antenna 635. While a control panel or a control device (e.g., 605) may include a single antenna 635, the control panel or the control device may also have multiple antennas 635 capable of concurrently transmitting or receiving multiple wired and/or wireless transmissions. In some embodiments, one element of control panel 665 (e.g., one or more antennas 635, transceiver module 630, etc.) may provide a connection using wireless techniques, including digital cellular telephone connection, Cellular Digital Packet Data (CDPD) connection, digital satellite data connection, and/or another connection.

The signals associated with system 600 may include wireless communication signals such as radio frequency, electromagnetics, local area network (LAN), wide area network (WAN), virtual private network (VPN), wireless network (using 302.11, for example), 345 MHz, Z-WAVE®, cellular network (using 3G and/or LTE, for example), and/or other signals. The one or more antennas 635 and/or transceiver module 630 may include or be related to, but are not limited to, WWAN (GSM, CDMA, and WCDMA), WLAN (including BLUETOOTH® and Wi-Fi), WMAN (WiMAX), antennas for mobile communications, antennas for Wireless Personal Area Network (WPAN) applications (including RFID and UWB). In some embodiments, each antenna 635 may receive signals or information specific and/or exclusive to itself. In other embodiments, each antenna 635 may receive signals or information not specific or exclusive to itself.

In some embodiments, one or more electrodes 660 (e.g., voltage, inductance, resistance, current, force, temperature, etc.) or devices 650 may connect to some element of system 600 via a network using one or more wired and/or wireless connections. In some embodiments, the user interface module 625 may include an audio device, such as an external speaker system, an external display device such as a display screen, and/or an input device (e.g., remote control device interfaced with the user interface module 625 directly and/or through I/O controller module 620).

One or more buses 640 may allow data communication between one or more elements of control panel 665 (e.g., processor module 605, memory 610, I/O controller module 620, user interface module 625, etc.).

The memory 610 may include random access memory (RAM), read only memory (ROM), flash RAM, and/or other types. The memory 610 may store computer-readable, computer-executable software/firmware code 615 including instructions that, when executed, cause the processor module 605 to perform various functions described in this disclosure (e.g., initiating an adjustment of a lighting system, etc.). Alternatively, the software/firmware code 615 may not be directly executable by the processor module 605 but may cause a computer (e.g., when compiled and executed) to perform functions described herein. Alternatively, the computer-readable, computer-executable software/firmware code 615 may not be directly executable by the processor module 605 but may be configured to cause a computer (e.g., when compiled and executed) to perform functions described herein. The processor module 605 may include an intelligent hardware device, e.g., a central processing unit (CPU), a microcontroller, an application-specific integrated circuit (ASIC), etc.

In some embodiments, the memory 610 can contain, among other things, the Basic Input-Output system (BIOS) which may control basic hardware and/or software operation such as the interaction with peripheral components or devices. For example, the sequencing module 645, and other modules and operational components of the control panel 665 used to implement the present systems and methods may be stored within the system memory 610. Applications resident with system 600 are generally stored on and accessed via a non-transitory computer readable medium, such as a hard disk drive or other storage medium. Additionally, applications can be in the form of electronic signals modulated in accordance with the application and data communication technology when accessed via a network interface (e.g., transceiver module 630, one or more antennas 635, etc.).

Many other devices and/or subsystems may be connected to one or may be included as one or more elements of system 600. In some embodiments, all of the elements shown in FIG. 8 need not be present to practice the present systems and methods. The devices and subsystems can be interconnected in different ways from that shown in FIG. 8. In some embodiments, an aspect of some operation of a system, such as that shown in FIG. 8, may be readily known in the art and are not discussed in detail in this application. Code to implement the present disclosure can be stored in a non-transitory computer-readable medium such as one or more of system memory 610 or other memory. The operating system provided on I/O controller module 620 may be iOS®, ANDROID®, MS-DOS®, MS-WINDOWS®, OS/2®, UNIX®, LINUX®, or another known operating system.

The transceiver module 630 may include a modem configured to modulate the packets and provide the modulated packets to the antennas 635 for transmission and/or to demodulate packets received from the antennas 635. While the control panel or control device (e.g., 605) may include a single antenna 635, the control panel or control device (e.g., 605) may have multiple antennas 635 capable of concurrently transmitting and/or receiving multiple wireless transmissions.

In some embodiments, the DNA sequencing device and systems described herein may be used to collect electronic signals associated with the nucleotides of a DNA strand passing through the gap between electrode pairs, and the collected electronic signals are processed at a different location. The processing may include electronically comparing the collected electronic signals to ranges of electronic signals associated with specific nucleotide types which have been previously determined and stored. In other embodiments, the DNA sequencing device includes capability of processing the collected electronic signals, conducting such comparison evaluations, and even formulating an order or sequence for the nucleotides of the DNA strand being evaluated.

While the examples disclosed herein are related to a four-letter DNA sequence, the principles disclosed herein may be applicable to other types of DNA strands with other numbers of nucleotides and/or types of nucleotides. The use of dyes and/or peptides to attach at specific sites/nucleotides of a given DNA strand may generally provide enhanced discrimination and/or identification of that particular type of nucleotide on any DNA or RNA strand.

INCORPORATION BY REFERENCE

The entire content of each of the previously filed provisional patent applications listed below are incorporated by reference in their entireties into this document, as are the related non-provisional patent applications of the same title filed concurrently with the present application. If the same term is used in both this document and one or more of the incorporated documents, then it should be interpreted to have the broadest meaning imparted by any one or combination of these sources unless the term has been explicitly defined to have a different meaning in this document. If there is an inconsistency between any of the following documents and this document, then this document shall govern. The incorporated subject matter should not be used to limit or narrow the scope of the explicitly recited or depicted subject matter.

- U.S. Prov. App. No. 62/453,270, titled "SINGLE-MOLECULE DNA SEQUENCING METHOD USING CONFINED NANO-FLUIDIC CHANNEL AND SUB-NANOMETER ELECTRODE GAP," filed on 1 Feb. 2017, and U.S. patent application Ser. No. 15/886,442, titled "SINGLE-MOLECULE DNA SEQUENCING METHOD USING CONFINED NANO-FLUIDIC CHANNEL AND SUB-NANOMETER ELECTRODE GAP," filed on 1 Feb. 2018.
- U.S. Prov. App. No. 62/453,398, titled "NANOFLUIDIC CHANNEL OPENING SIZE CONTROL USING ACTUATION," filed on 1 Feb. 2017, and U.S. patent application Ser. No. 15/886,483, titled "NANOFLUIDIC CHANNEL OPENING SIZE CONTROL USING ACTUATION," filed on 1 Feb. 2018.
- U.S. Prov. App. No. 62/453,298, titled "FABRICATION OF NANOCHANNEL WITH INTEGRATED ELECTRODES FOR DNA SEQUENCING USING TUNNELING CURRENT," filed on 1 Feb. 2017, and U.S. patent application Ser. No. 15/886,511, titled "FABRICATION OF NANOCHANNEL WITH INTEGRATED ELECTRODES FOR DNA SEQUENCING USING TUNNELING CURRENT," filed on 1 Feb. 2018.
- U.S. Prov. App. No. 62/453,307, titled "METHOD TO FABRICATE A NANOCHANNEL FOR DNA SEQUENCING BASED ON NARROW TRENCH PATTERNING PROCESS," filed on 1 Feb. 2017, and U.S. patent application Ser. No. 15/886,533, titled "METHOD TO FABRICATE A NANOCHANNEL FOR DNA SEQUENCING BASED ON NARROW TRENCH PATTERNING PROCESS," filed on 1 Feb. 2018.
- U.S. Prov. App. No. 62/453,323, titled "FABRICATION OF A DEVICE FOR SINGLE-MOLECULE DNA SEQUENCING USING SIDEWALL LITHOGRAPHY," filed on 1 Feb. 2017, and U.S. patent application Ser. No. 15/886,560, titled "FABRICATION OF A DEVICE FOR SINGLE-MOLECULE DNA SEQUENCING USING SIDEWALL LITHOGRAPHY," filed on 1 Feb. 2018.

U.S. Prov. App. No. 62/453,339, titled "FABRICATION OF A NANOCHANNEL FOR DNA SEQUENCING USING ELECTRICAL PLATING TO ACHIEVE TUNNELING ELECTRODE GAP," filed on 1 Feb. 2017, and U.S. patent application Ser. No. 15/886,581, titled "FABRICATION OF A NANOCHANNEL FOR DNA SEQUENCING USING ELECTRICAL PLATING TO ACHIEVE TUNNELING ELECTRODE GAP," filed on 1 Feb. 2018.

U.S. Prov. App. No. 62/453,346, titled "NANOSTRUCTURES TO CONTROL DNA STRAND ORIENTATION AND POSITION LOCATION FOR TRANSVERSE DNA SEQUENCING," filed on 1 Feb. 2017, and U.S. patent application Ser. No. 15/886,608, titled "NANOSTRUCTURES TO CONTROL DNA STRAND ORIENTATION AND POSITION LOCATION FOR TRANSVERSE DNA SEQUENCING," filed on 1 Feb. 2018.

U.S. Prov. App. No. 62/453,365, titled "FABRICATION OF WEDGE SHAPED ELECTRODE FOR ENHANCED DNA SEQUENCING USING TUNNELING CURRENT," filed on 1 Feb. 2017, and U.S. patent application Ser. No. 15/886,661, titled "FABRICATION OF WEDGE SHAPED ELECTRODE FOR ENHANCED DNA SEQUENCING USING TUNNELING CURRENT," filed on 1 Feb. 2018.

U.S. Prov. App. No. 62/453,329, titled "DIRECT SEQUENCING DEVICE WITH A TOP-BOTTOM ELECTRODE PAIR," filed on 1 Feb. 2017, and U.S. patent application Ser. No. 15/886,685, titled "DIRECT SEQUENCING DEVICE WITH A TOP-BOTTOM ELECTRODE PAIR," filed on 1 Feb. 2018.

U.S. Prov. App. No. 62/453,376, titled "MICRO AND NANOFLUIDIC CHANNEL CONTROLLED ACTUATION TO OPEN CHANNEL GAP," filed on 1 Feb. 2017.

U.S. Prov. App. No. 62/469,409, titled "VERTICAL NANOPORE COUPLED WITH A PAIR OF TRANSVERSE ELECTRODES HAVING A UNIFORM ULTRASMALL NANOGAP FOR DNA SEQUENCING," filed on 9 Mar. 2017, and U.S. patent application Ser. No. 15/886,723, titled "VERTICAL NANOPORE COUPLED WITH A PAIR OF TRANSVERSE ELECTRODES HAVING A UNIFORM ULTRASMALL NANOGAP FOR DNA SEQUENCING," filed on 9 Mar. 2018.

The detailed description set forth above in connection with the appended drawings describes examples and does not represent the only instances that may be implemented or that are within the scope of the claims. The terms "example" and "exemplary," when used in this description, mean "serving as an example, instance, or illustration," and not "preferred" or "advantageous over other examples." The detailed description includes specific details for the purpose of providing an understanding of the described techniques. These techniques, however, may be practiced without these specific details. In some instances, known structures and apparatuses are shown in block diagram form in order to avoid obscuring the concepts of the described examples.

As used herein, including in the claims, the term "and/or," when used in a list of two or more items, means that any one of the listed items can be employed by itself, or any combination of two or more of the listed items can be employed. For example, if a composition is described as containing components A, B, and/or C, the composition can contain A alone; B alone; C alone; A and B in combination; A and C in combination; B and C in combination; or A, B, and C in combination. Also, as used herein, including in the claims, "or" as used in a list of items (for example, a list of items prefaced by a phrase such as "at least one of" or "one or more of") indicates a disjunctive list such that, for example, a list of "at least one of A, B, or C" means A or B or C or AB or AC or BC or ABC (i.e., A and B and C).

In addition, any disclosure of components contained within other components or separate from other components should be considered exemplary because multiple other architectures may potentially be implemented to achieve the same functionality, including incorporating all, most, and/or some elements as part of one or more unitary structures and/or separate structures.

The previous description of the disclosure is provided to enable a person skilled in the art to make or use the disclosure. Various modifications to the disclosure will be readily apparent to those skilled in the art, and the generic principles defined herein may be applied to other variations without departing from the scope of the disclosure. Thus, the disclosure is not to be limited to the examples and designs described herein but is to be accorded the broadest scope consistent with the principles and novel features disclosed.

The process parameters, actions, and steps described and/or illustrated in this disclosure are given by way of example only and can be varied as desired. For example, while the steps illustrated and/or described may be shown or discussed in a particular order, these steps do not necessarily need to be performed in the order illustrated or discussed. The various exemplary methods described and/or illustrated here may also omit one or more of the steps described or illustrated here or include additional steps in addition to those disclosed.

This description, for purposes of explanation, has been described with reference to specific embodiments. The illustrative discussions above, however, are not intended to be exhaustive or limit the present systems and methods to the precise forms discussed. Many modifications and variations are possible in view of the above teachings. The embodiments were chosen and described in order to explain the principles of the present systems and methods and their practical applications, to enable others skilled in the art to utilize the present systems, apparatus, and methods and various embodiments with various modifications as may be suited to the particular use contemplated.

What is claimed is:

1. A method of identifying nucleotides of a DNA strand, the method comprising:
    exposing the DNA strand to a first dye or peptide;
    attaching the first dye or peptide to a first type of nucleotide (A,T,C,G) of the DNA strand, the first dye or peptide changing a conductance of the first type of nucleotide to which the first dye or peptide is attached;
    measuring a tunneling current signal for all nucleotides of the DNA strand, the changed conductance of the first type of nucleotide providing amplified tunneling current discrimination of the nucleotides of the DNA strand.

2. The method of claim 1, wherein the first type of nucleotide is an A (Adenine) nucleotide or a C (Cytosine) nucleotide.

3. The method of claim 1, further comprising:
    exposing the DNA strand to a second dye or peptide;
    attaching the second dye or peptide to a second type of nucleotide (A,T,C,G) of the DNA strand, the second dye or peptide changing a conductance of the second type of nucleotide to which the second dye or peptide is attached;

wherein the changed conductance of the second type of nucleotide provides amplified tunneling current discrimination of the nucleotides of the DNA strand when measuring the tunneling current signal for all nucleotides of the DNA strand.

4. The method of claim 1, wherein the change in conductance is a reduction in conductance.

5. The method of claim 4, wherein the reduction in conductance results in an increased tunneling current signal for the first type of nucleotide.

6. The method of claim 4, wherein the reduction in conductance is to a reduced conductance level that is less than a conductance level for all other types of nucleotides of the DNA strand.

7. A method of DNA sequencing, comprising:
providing a plurality of channels, each channel comprising at least one tunneling electrode;
exposing a first DNA strand to a first dye or peptide, and attaching the first dye or peptide to a first type of nucleotide (A,T,C,G) of the first DNA strand, the attached first dye or peptide changing a conductance of the first type of nucleotide;
exposing a second DNA strand to a second dye or peptide, and attaching the second dye or peptide to a second type of nucleotide (A,T,C,G) of the second DNA strand, the attached second dye or peptide changing a conductance of the second type of nucleotide;
exposing a third DNA strand to a third dye or peptide, and attaching the third dye or peptide to a third type of nucleotide (A,T,C,G) of the third DNA strand, the attached third dye or peptide changing a conductance of the third type of nucleotide;
passing the first, second and third DNA strands through separate ones of the plurality of DNA sequencing channels;
measuring a tunneling current for the nucleotides with attached dyes or peptides in each of the channels, the measured tunneling currents being used to identify a location of the nucleotides with attached dyes or peptides on each DNA strand;
determining a sequence for the nucleotides of the DNA strands using the identified locations for the nucleotides with attached dyes or peptides.

8. The method of claim 7, wherein the plurality of channels includes four channels, the method further comprising:
exposing a fourth DNA strand to a fourth dye or peptide, and attaching the fourth dye or peptide to a fourth type of nucleotide (A,T,C,G) of the fourth DNA strand, the attached fourth dye or peptide changing a conductance of the fourth type of nucleotide;
passing the fourth DNA strand through one of the plurality of DNA sequencing channels.

9. The method of claim 7, wherein the plurality of DNA sequencing channels includes three DNA sequencing channels, and the plurality of DNA strands includes three DNA strands.

10. The method of claim 9, wherein the locations for the first, second and third types of nucleotides are used to construct a partial DNA sequence, and locations for a fourth nucleotide are determined by process of elimination.

11. The method of claim 7, wherein changing the conductance of the first, second and third types of nucleotides includes reducing the conductance.

12. The method of claim 11, wherein the reduction in conductance results in an increased tunneling current signal.

13. The method of claim 7, wherein the DNA strands each have identical DNA sequencing.

14. A DNA sequencing method, comprising:
amplifying tunneling current discrimination of nucleotides of a DNA strand using attachment of dyes or peptides to at least one specific type of nucleotide (A,T,C,G) of the DNA strand.

15. The method of claim 14, wherein the dyes or peptides change a conductance value for the nucleotide to which the dyes or peptides are attached, and the changed conductance results in a changed tunneling current value for the nucleotides to which the dyes or peptides are attached.

16. The method of claim 14, wherein the type of nucleotide is one of an A (Adenine) nucleotide or a C (Cytosine) nucleotide.

17. The method of claim 14, further comprising determining at least a portion of a DNA sequence using the amplified transverse tunneling current discrimination.

18. The method of claim 14, further comprising:
exposing the DNA strand to a first dye or peptide;
attaching the first dye or peptide to a first type of nucleotide (A,T,C,G) of the DNA strand, the first dye or peptide changing the conductance of the first type of nucleotide to which the first dye or peptide is attached;
measuring a tunneling current signal for all nucleotides of the DNA strand, the changed conductance of the first type of nucleotide providing amplified tunneling current discrimination of the nucleotides of the DNA strand.

19. The method of claim 15, further comprising:
exposing the DNA strand to a second dye or peptide;
attaching the second dye or peptide to a second type of nucleotide (A,T,C,G) of the DNA strand, the second dye or peptide changing the conductance of the second type of nucleotide to which the second dye or peptide is attached.

20. The method of claim 18, wherein the change in conductance is a reduction in conductance, the reduction in conductance providing an increased tunneling current signal for the first type of nucleotide.

* * * * *